US007776790B2

(12) United States Patent  
Herold et al.

(10) Patent No.: US 7,776,790 B2
(45) Date of Patent: *Aug. 17, 2010

(54) HERBICIDE COMPOSITIONS COMPRISING SUSPENSION CONCENTRATE WITH GLYPHOSATE ACID, METHODS OF PREPARATION, AND METHODS OF USE

(75) Inventors: Anthony E. Herold, Greeley, CO (US); Richard A. Beardmore, Windsor, CO (US); Scott K. Parrish, Spokane, WA (US)

(73) Assignee: Platte Chemical Co., Greeley, CO (US)

( * ) Notice: Subject to any disclaimer, the term of this patent is extended or adjusted under 35 U.S.C. 154(b) by 1182 days.

This patent is subject to a terminal disclaimer.

(21) Appl. No.: 10/103,493

(22) Filed: Mar. 21, 2002

(65) Prior Publication Data

US 2003/0153462 A1 Aug. 14, 2003

Related U.S. Application Data

(60) Provisional application No. 60/325,289, filed on Sep. 26, 2001, provisional application No. 60/325,342, filed on Sep. 26, 2001, provisional application No. 60/325,343, filed on Sep. 26, 2001, provisional application No. 60/361,016, filed on Feb. 28, 2002.

(51) Int. Cl.
*A01N 25/30* (2006.01)
*A01N 57/02* (2006.01)

(52) U.S. Cl. .................... 504/206; 504/363
(58) Field of Classification Search .................. 504/206
See application file for complete search history.

(56) References Cited

U.S. PATENT DOCUMENTS

| 3,755,339 | A | 8/1973 | McKendry ............... 260/295 R |
| 3,761,486 | A | 9/1973 | McGregor ............... 260/294.9 |
| 3,937,826 | A | 2/1976 | Harris ..................... 424/219 |
| 4,445,925 | A | 5/1984 | Young ..................... 71/28 |
| 4,971,630 | A | 11/1990 | Skaptason ................ 71/117 |
| 4,994,101 | A | 2/1991 | Young ..................... 71/83 |
| 5,118,338 | A | 6/1992 | Moller .................... 71/86 |
| 5,189,414 | A | 2/1993 | Tawara .................... 340/825.5 |
| 5,221,319 | A | 6/1993 | Van Haften et al. ......... 504/144 |
| 5,268,352 | A | 12/1993 | Dexter .................... 504/206 |
| 5,270,286 | A | 12/1993 | Ong ....................... 504/130 |
| 5,280,008 | A | 1/1994 | Cahoy et al. .............. 504/116 |
| 5,288,692 | A * | 2/1994 | Young ..................... 504/127 |
| 5,317,042 | A | 5/1994 | Narayanan ................ 514/722 |
| 5,328,889 | A | 7/1994 | Van Haften et al. ......... 504/116 |
| 5,416,067 | A | 5/1995 | Van Haften et al. ......... 504/323 |
| 5,498,773 | A | 3/1996 | Noveroske et al. |
| 5,538,936 | A | 7/1996 | Hermansky |
| 5,565,409 | A | 10/1996 | Sato et al. ................ 504/127 |
| 5,668,085 | A | 9/1997 | Forbes et al. ............. 504/206 |
| 5,707,928 | A | 1/1998 | Baker ..................... 504/139 |
| 5,741,502 | A | 4/1998 | Roberts |
| 5,877,112 | A | 3/1999 | Roberts et al. |
| 5,994,271 | A | 11/1999 | Ravetta et al. ............. 504/206 |
| 6,069,115 | A | 5/2000 | Pallett et al. ............. 504/270 |
| 6,071,857 | A | 6/2000 | Vogt et al. ................ 504/116 |
| 6,127,317 | A | 10/2000 | De Carvalao Castro et al. |
| 6,156,705 | A | 12/2000 | Mueninghoff |
| 6,165,939 | A | 12/2000 | Agbaje et al. ............. 504/105 |
| 6,180,563 | B1 | 1/2001 | Ruegg et al. .............. 504/128 |
| 6,180,566 | B1 | 1/2001 | Nielsen et al. ............. 504/206 |
| 6,187,715 | B1 | 2/2001 | Narayanan et al. .......... 504/118 |
| 6,207,617 | B1 | 3/2001 | Gillespie ................. 504/206 |
| 6,232,272 | B1 | 5/2001 | Roberts et al. |
| RE37,313 | E | 8/2001 | Roberts |
| 6,541,424 | B2 | 4/2003 | Roberts et al. |
| 2001/0034304 | A1 | 10/2001 | Volgas et al. |
| 2002/0039970 | A1 * | 4/2002 | Roberts et al. ............. 504/206 |
| 2002/0107149 | A1 | 8/2002 | Volgas et al. .............. 504/317 |
| 2002/0108415 | A1 | 8/2002 | Volgas et al. |
| 2002/0160916 | A1 | 10/2002 | Volgas et al. |

FOREIGN PATENT DOCUMENTS

| CA | 1225533 | 8/1987 |
| DE | 2 328 192 | 1/1974 |
| EP | 0 100 440 | 2/1984 |
| EP | 0 163 598 | 4/1985 |
| EP | 0 216 126 | 4/1987 |
| EP | 0 217 125 | 4/1987 |
| EP | 0 243 522 | 11/1987 |
| EP | 0334041 | 9/1989 |
| EP | 0 357 553 | 3/1990 |
| EP | 0 433 577 | 6/1991 |
| EP | 0 454 968 | 11/1991 |
| EP | 0 512 739 A1 | 11/1992 |
| EP | 0512739 | 11/1992 |
| EP | 0 641 161 | 10/1996 |

(Continued)

OTHER PUBLICATIONS

PCT/US02/08830 International Search Report.
PCT/US02/08787 International Search Report.
PCT/US02/08952 Annex to Form PCT/ISA/206 Communication Relating to the Results of the Partial International Search.
PCT/US02/08953 Annex to Form PCT/ISA/206, Communication Relating to the Results of the Partial International Search.
Milton J. Rosen, "Surfactants and Interfacial Phenomena," John Wiley & Sons, pp. 239-240 (1978).
Briggs et al., "Physico-chemical Factors Affecting Uptake by Roots and Translocation to Shoots of Weak Acids in Barley," *Pesticide Science*, vol. 19, pp. 101-112 (1987).
Wyrill, J.B. et al., "Glyphosate Toxicity to Common Milkweed and Hemp Dogbane as Influenced by Surfactants," Weed Science, vol. 25, No. 3 pp. 275-287 (May 1977).
Tomlin, C., Ed., The Pesticide Manual, Tenth Edition, p. 1338, (1995).
Chemical Abstracts, Turner et al., "Complexing agents as herbicide additives," Weed Res., vol. 18, No. 4, pp. 199-207 (1978), CA 89: 158688.

(Continued)

*Primary Examiner*—Yong S Chong
(74) *Attorney, Agent, or Firm*—Faegre & Benson LLP

(57) ABSTRACT

Described are suspension concentrates that include glyphosate acid, herbicide compositions prepared therefrom, and methods of making and using each.

28 Claims, No Drawings

FOREIGN PATENT DOCUMENTS

| | | |
|---|---|---|
| EP | 0 703 724 | 2/2002 |
| GB | 2 230 955 | 11/1990 |
| GB | 2267825 | 12/1993 |
| WO | WO 92/21686 | 12/1992 |
| WO | WO94/19941 | 9/1994 |
| WO | WO96/08150 | 3/1996 |
| WO | WO98/17109 | 4/1998 |
| WO | WO99/55155 | 11/1999 |
| WO | WO00/42847 | 7/2000 |
| WO | WO00/67571 | 11/2000 |
| WO | WO01/52650 | 7/2001 |
| WO | WO02/11536 | 2/2002 |
| WO | WO 03/103396 A1 | 12/2003 |

OTHER PUBLICATIONS

Chemical Abstracts, McMullan, "Effect of adjuvant and acidifying agent on imazamethabenz efficacy," Can. J. Plant Sci., vol. 72, No. 4, pp. 1389-1392 (1992), CA 108: 207455.

Chemical Abstracts, Zsoldos et al., "Effects of ph changes on ion and 2,4-D uptake of wheat roots," Dep. Plant Physiol., pp. 77-80 (1978), CA 92: 192532.

Chemical Abstracts, Shone et al., "Absorption and translocation of 2,4-dichlorophenoxyacetic acid (2,4-D) by barley roots," Annu. Rep.—Agric. Res. Counc., pp. 32-33 (1973), CA 85: 57935.

Chemical Abstracts, Sherrick et al., "Effects of adjuvants and environment during plant development on glyphosate adsorption and translocation in field bindweed," Weed Sci., vol. 34, No. 6, pp. 811-816 (1986), CA 106: 14601.

PCT/US02/08952 International Search Report.

PCT/US02/08953 International Search Report.

* cited by examiner

HERBICIDE COMPOSITIONS COMPRISING SUSPENSION CONCENTRATE WITH GLYPHOSATE ACID, METHODS OF PREPARATION, AND METHODS OF USE

This application claims the benefit of U.S. Provisional Application Ser. No. 60/325,289, U.S. Provisional Application Ser. No. 60/325,342, and U.S. Provisional Application Ser. No. 60/325,343, all filed Sep. 26, 2001, and the benefit of U.S. Provisional Application Ser. No. 60/361,016, entitled Herbicide Compositions Comprising Imidazolinone Acid, Methods of Preparation, and Methods of Use, filed Feb. 28, 2002.

FIELD OF THE INVENTION

The invention relates to compositions comprising suspension concentrates and other herbicide compositions that contain glyphosate acid, methods of preparing such suspension concentrates and herbicide compositions, and methods of using each.

BACKGROUND

Commercially available herbicide compositions include a very large variety of active herbicide compounds. Such herbicide compositions can be prepared from different types of precursor compositions, and can be commercially available and used in a variety of different types of compositions, including, for example, compositions referred to as wettable powders, water dispersible granules, granules, aqueous solutions, water soluble powders, emulsifiable concentrates, oil-based flowables, concentrated emulsions, suspo-emulsions, emulsions, suspensions, suspension concentrates, mixtures, dispersions, and microemulsions, as well as others. Any of these different types of compositions may have different advantages or disadvantages relating to factors such as the mode of application and the type of active ingredient included in the herbicide composition.

Examples of just a few available active herbicide compounds include those of the general class known as phenoxy herbicides, e.g., 2,4-dichlorophenoxyacetic acid (known as 2,4-D), MCPA acid, MCPP acid; those of the general class known as pyridine herbicides, (e.g., triclopyr, fluoroxypyr); those of the general class of benzoic acid herbicides, (e.g., dicamba acid); those of the general class of aryloxy phenoxy propionic acid herbicides, (e.g., fluzafop acid and quizolofop acid); water-insoluble diphenyl ether type herbicides (e.g., oxyfluorfen or acifluorfen); glyphosate compounds (N-(phosphonomethyl)glycine), e.g., in the acid form, referred to as glyphosate acid, or in a salt form such as the IPA salt form; imidizole herbicide compounds (e.g., imazapyr or imazaquin); as well as others.

Active herbicide ingredients such as these and others can be prepared from and used in the form of solid and liquid compositions including, as mentioned above, different forms of emulsions, suspensions, suspension concentrates, mixtures, dispersions, microemulsions, etc., and derivatives thereof such as diluted solutions or solutions including other added ingredients such as additional herbicides.

Specifically with regard to herbicide compounds containing N-(phosphonomethyl)glycine, this compound is understood to be available in a variety of chemically different forms including glyphosate acid and glyphosate salts. These glyphosate compounds are described as being useful in herbicide compositions in their salt form, or as glyphosate acid, in combination with specific surfactants as a water-soluble free-flowing solid formulation. See, for example, U.S. Pat. Nos. 5,118,338, 5,668,085, and 5,994,271. The salts of glyphosate, e.g., ammonium, sodium, isopropylammonium, and trimesium, are considered to be very soluble in water, while the acid form is not.

New forms of effective herbicide compositions are always desirable, especially those that can show advantages in processing, application, environmental profile (e.g., volatility), or efficacy.

SUMMARY OF THE INVENTION

The invention relates to suspension concentrates that include the herbicide compound glyphosate acid, in the acid form, and derivatives and uses of those suspension concentrates. The suspension concentrates can be used in their suspension concentrate form to control plant growth, or can be used to prepare derivative herbicide compositions for application to control plant growth. For example, the suspension concentrate can be combined with an acidifying agent, e.g., in a tank mix procedure or otherwise, to form a herbicide application composition, and can optionally be further combined with other ingredients such as an additional, different active herbicide compound. Preferred herbicide application compositions can have a pH below about 2.6 or 2.3, or otherwise below the pKa of glyphosate acid compound.

The suspension concentrate has been found to be easily and efficiently producible with the use of one or more other ingredients such as surfactants (wetting agents), dispersants, thickeners, etc., one or more of which optionally in combination with one or more of mixing, agitation, and milling, etc., can allow glyphosate acid particles to be suspended and/or dispersed in water to form a suspension concentrate.

The use of a herbicide composition containing glyphosate in the acid form provides efficiency because the acid form does not need to be converted to the glyphosate salt form during processing or prior to application, as is often done with the glyphosate herbicide compound (because the salt forms are more soluble in water). Instead, the suspension concentrate of the invention, including the glyphosate acid herbicide in its glyphosate acid form, is simple and economical to produce, and can be efficiently distributed, prepared, and applied without taking steps to convert the glyphosate herbicide out of its acid form. The invention can also advantageously provide improved efficacy of the glyphosate acid herbicide compound, especially when used in combination with acidifying agents. The glyphosate acid suspension concentrates have other benefits when compared to other herbicide formulations such as the absence of dust; reduction of toxicity or flammability, etc.; they do not require organic solvents; they can exhibit increased efficacy, for example due to lower particle size; they benefit from a low packing volume as compared to other forms of herbicides such as powers; and the suspension concentrates are relatively easy to handle.

In addition, the acid form of glyphosate acid, due to its uncharged state, can be advantageously less affected or unaffected by hard water, e.g., less susceptible to de-activation by hard water.

An aspect of the invention relates to a suspension concentrate comprising glyphosate acid particles suspended in water and surfactant selected from the group consisting of cationic surfactant, anionic surfactant, and mixtures thereof.

Another aspect of the invention relates to suspension concentrates comprising glyphosate acid and short chain alcohol ethoxylate nonionic surfactant, e.g., having a short chain branched or linear alkyl having from 3 to 23 or fewer carbon atoms.

Yet another aspect of the invention relates to a herbicide composition comprising a suspension concentrate comprising glyphosate acid, and acidifying agent other than sulfuric acid in an amount so the pH of the herbicide composition is below the pKa of glyphosate acid.

Another aspect of the invention relates to a herbicide composition comprising a suspension concentrate comprising glyphosate acid. The herbicide composition also includes acidifying agent other than sulfuric acid, in an amount so the pH of the herbicide composition is below the pKa of glyphosate acid.

Another aspect of the invention relates to a method of applying a herbicide composition, the method comprising: preparing a herbicide composition comprising a suspension concentrate comprising glyphosate acid, and acidifying agent other than sulfuric acid, the acidifying agent being included in an amount so that the pH of the herbicide composition is below the pKa of glyphosate acid; and applying the herbicide composition to control plant growth.

Still another aspect of the invention relates to a method of preparing a suspension concentrate comprising glyphosate acid. The method comprises: combining glyphosate acid particles with water and surfactant selected from anionic surfactant, cationic surfactant, short chain alcohol ethoxylate nonionic surfactant, and mixtures thereof; and mixing or agitating the water, glyphosate acid particles, and surfactant to produce a suspension concentrate.

Still a further aspect of the invention relates to a method of preparing a suspension concentrate comprising glyphosate acid. The method comprises: combining glyphosate acid particles with water, surfactant, and dispersant; wet milling the mixture of glyphosate acid particles, water, surfactant, and dispersant, to reduce the size of glyphosate acid particles to a size that can be suspended in the water, surfactant, and dispersant; and using a high speed mixer to mix the water, glyphosate acid, particles, surfactant, and dispersant, to produce a suspension concentrate comprising the glyphosate acid particles.

Yet another aspect of the invention relates to a method of preparing a herbicide composition comprising glyphosate acid. The method comprises preparing a suspension concentrate composition by a method comprising: combining glyphosate acid particles with water and one or more of surfactant and dispersant; mixing or agitating the water, glyphosate acid particles, and one or more of surfactant and dispersant, to produce a suspension concentrate containing the glyphosate acid particles; and combining the suspension concentrate composition with acidifying agent other than sulfuric acid.

DETAILED DESCRIPTION

Glyphosate (N-(phosphonomethyl)glycine) compounds (or "glyphosate"), and chemical derivatives thereof, are a known type of active herbicide compound. Glyphosate is generally considered a broad spectrum, post-emergent, systemic herbicide effective for the control of many annual and perennial grasses and broadleaf weeds, in addition to many tree and wooden brush species both in cropland and noncrop sites. Glyphosate is available in the acid form, referred to as glyphosate acid, and is also available and more commonly used for herbicide application in its various salt forms, such as its isopropylamine (IPA) salt form. These salt forms are considered to be generally soluble in water, which encourages the use of the glyphosate salt forms. Glyphosate is sold as the isopropylamine salt under the trade name Roundup®.

The invention relates to herbicide compositions that include glyphosate acid, i.e., glyphosate (N-(phosphonomethyl)glycine), in the acid form. The term "herbicide composition" refers to compositions that include a herbicide compound, specifically here, glyphosate acid. Herbicide compositions include the described suspension concentrates and derivatives thereof.

Glyphosate acid is generally considered to be an insoluble active herbicide compound. This means, for example, depending on temperature and pH, that glyphosate acid can be soluble in water or acidic water only up to a few weight percent, meaning that approximately 100 grams of an aqueous solution can dissolve only approximately a couple of grams of glyphosate acid, e.g., approximately 1 gram, or one weight percent. The glyphosate compound (N-(phosphonomethyl)glycine) includes 4 acidic protons which are removed at $pKa_1$ of 0.8 ($1^{st}$ phosphonic), $pKa_2$ 2.3 or 2.6 (carboxylate), $pKa_3$ 6.0 ($2^{nd}$ phosphonic), and $pKa_4$ 11.0 (amine). For purposes of the present description, when discussing the pKa of the glyphosate acid form of the N-(phosphonomethyl)glycine, the $pKa_2$ is specifically meant, because this is the pKa that relates to the conversion of the glyphosate compound to and from the protonated and deprotonated carboxylic acid form, which is generally considered to be the "acid" form of the glyphosate herbicide compound. See, for example, http://www.soils.wisc.edu/virtual_museum/glyphosate/glyphosate_tx.html, which is part of the Virtual Museum of Minerals and Molecules, originally released 25 Dec. 1999, and last modified 31 Dec. 2000.

Glyphosate acid is commercially available, generally in the form of a granular, solid, powder form or as a wet cake, for example from Dow Chemical Co., under the tradename Glyphosate WC. These materials are sold in the form of solid glyphosate acid particles having an average size (diameter) in the range from about 5 to about 18 microns.

According to the invention, glyphosate acid is incorporated into a suspension concentrate. The term "suspension concentrate" as used herein, means a composition also sometimes referred to as an "aqueous flowable" or a "water-based flowable" composition, which compositions are known in the herbicide art and include or consist of particles of a generally insoluble solid active herbicide compound in suspension (preferably concentrated suspension) in water.

The suspension concentrates described herein can be produced with particles of glyphosate acid by suspending and preferably dispersing the particles in water with the assistance of other ingredients such as conventional dispersants, surfactants (wetting agents), and other optional ingredients.

The glyphosate acid should be in the form of particles that exhibit physical characteristics such as size, shape, surface features, etc., that will allow the glyphosate acid particles to be suspended in water as described. The particle size range can vary depending on factors such as the other ingredients used to prepare the suspension concentrate and their respective amounts, but exemplary particles may be in the size range below about 10 microns, for example in the range from about 4 or 5 to about 7 or 8 microns.

The suspension concentrate includes water in a useful amount, such as an amount that, in combination with one or more other ingredients described herein (e.g., such as surfactant and/or dispersant) will allow suspension and preferably dispersion of the glyphosate acid particles. Relative amounts of water and the other ingredients used to prepare a suspension concentrate can be any amounts that produce a useful herbicide composition in the form of a suspension concentrate. Relative amounts of different ingredients (water, glyphosate acid, surfactant, etc.) in any particular composition can depend on the intended application (including the plant to be controlled or the crop to be protected), the mode of application (e.g., field or aerial spraying or application from a hand-held spray applicator, or other technique), the method of any preparation from a suspension concentrate to a herbicide application composition, the amounts and identities of other ingredients added to the suspension concentrate, etc. Useful amounts of water in a suspension concentrate may be, for example, in the range from about 20 to about 60 weight percent water based on the total weight of the suspension concentrate, such as from about 30 to about 50 weight percent water in a suspension concentrate.

A wetting agent (also referred to herein as "surfactant"), can be used to facilitate suspending the glyphosate acid particles in a suspension concentrate. Surfactants can lower the surface tension of the water, helping to replace air on the surface of particles of the glyphosate acid with water, thereby suspending the particles. During milling (see below), new particle surfaces are created by mechanical breakdown of solid glyphosate particles. The surfactant adsorbs onto the particle surfaces to give rise to fluidity of the suspension.

A very large variety of surfactants are known and commercially available, including such different classes as cationic surfactants, anionic surfactants, non-ionic surfactants, ionic surfactants, and amphoteric surfactants, etc. The surfactant can be a surfactant or combination of surfactants useful to suspend particles of glyphosate acid. Examples of some preferred surfactants include cationic, certain non-ionic surfactants, and anionic surfactants, either alone or in combinations (e.g., blends of cationic and nonionic surfactants). Of these, particular types of preferred surfactants include non-ionic linear or branched alcohol ethoxylate surfactants, anionic phosphoric acid ester surfactants (sometimes referred to as "phosphate ester" surfactants), and cationic ethoxylated tallow amine surfactants. An example of useful surfactant would include nonionic wetting agents such as Surfonic L12-6, from Huntsman. Other examples of commercially available surfactants of these general classes include the following:

Exemplary sodium alkyl naphthalene sulfonate surfactants include sodium butyl naphthalene sulfonate, sodium di-n-butyl naphthalene sulfonate, sodium diisopropyl naphthalene sulfonate, sodium dimethyl naphthalene sulfonate, and mixtures thereof. Sodium butyl naphthalene sulfonate is commercially available, for example, under the trade name "MORWET B" from Witco/Crompton, Greenwich, Conn. Sodium di-n-butyl naphthalene sulfonate is commercially available, for example, under the trade name "MORWET DB" from Witco/Crompton, Greenwich, Conn. Sodium diisopropyl naphthalene sulfonate is commercially available, for example, under the trade name "MORWET IP" from Witco/Crompton, Greenwich, Conn. Sodium dimethyl naphthalene sulfonate surfactant is commercially available, for example, under the trade name "SELLOGEN HR" from Henkle Corp., Cincinnati, Ohio.

An exemplary ethoxylated tristyrylphenol phosphate potassium salt surfactant is commercially available, for example, under the trade name "SOPROPHOR FLK" from Rhodia, Cranbury, N.J.

A nonionic surfactant is a surface-active molecule that does not contain ionizable polar end groups but does contain hydrophilic and lipophilic portions. Exemplary nonionic surfactants include polyoxyethylene alkylether or alkenylether surfactants. Nonionic surfactant used to prepare a suspension concentrate as described herein may include long or short chain alcohol ethoxylate surfactant. The alcohol ethoxylate surfactant may be branched or linear.

An example of a useful nonionic polyoxyalkylene surfactant includes alcohol ethoxylate having the general formula:

$$R-O-((CH_2)_xO)_y-H$$

wherein R may be "long" or "short chain" and "branched" or "linear" alkyl. R preferably can be a "short chain" branched or linear alcohol, meaning that it can have from about 3 to 23 or fewer carbon atoms. With respect to the oxyalkylene, x can preferably be in the range from about 2 to 5, preferably from

| TRADE NAME | COMMON NAME | FUNCTION | GENERAL CLASSIFICATION |
|---|---|---|---|
| Tomadol 1-5 | 11 carbon 5 mole linear alcohol | wetting agent | nonionic |
| Surfonic L12-6 | 12 carbon 6 mole linear alcohol | wetting agent | nonionic |
| Trymeen 6607 | 20 mole tallow amine | wetting agent/adjuvant | cationic |
| Stepfac 8170 | phosphate ester | dispersant/adjuvant | anionic |
| Surfonic PE 1218 | phosphate ester | dispersant/adjuvant | anionic |
| Surfonic OP-70 | 7 mole octylphenol | wetting agent/adjuvant | nonionic |
| Tergitol NP-9 | 9 mole nonylphenol | wetting agent/adjuvant | nonionic |
| Soprophor 796P | tristerol phenol EO/PO | dispersant | nonionic |
| Soprophor FLK | tristerolphenol potassium phosphate | dispersant | anionic |
| Polyfon H | sodium lignosulfonate | dispersant | anionic |
| Morwet D425 | napthalene formaldehyde condensant | dispersant | anionic |
| Morwet IP | naphthalene sulfonates | wetting agent | anionic |
| Pluronic L1061 | block copolymer | disperant | nonionic |
| Tersperse 4984 | block copolymer/alcohol ethoxylate | dispersant, wetting | nonionic |
| Tersperse 2500 | surfactant | dispersant | anionic |
| Surfonic DOS60 | sulfosuccinate | wetting agent | anionic |
| LI-700 | lecithin derivative | adjuvant | nonionic |
| Goodrite K732 | polyacrylic acid | dispersant | anionic |

An anionic surfactant is a surface-active molecule in which an active portion of a lipophilic portion of the molecule forms a negative ion (i.e., anion) when placed in aqueous solution. Exemplary anionic surfactants include phosphoric acid ester surfactants (sometimes referred to as "phosphate ester" surfactants), sodium alkyl naphthalene sulfonate surfactants, and ethoxylated tristyrylphenol phosphate salts.

about 2 to 4 (e.g., 2 or 3, for a polyoxyethylene or polyoxypropylene, respectively) and y can preferably be in the in the range from 5 to 25.

Examples of useful short chain nonionic polyoxyalkylenes include linear alcohol polyoxyethylenes having the general formula:

$$CH_3(C_2H_4)_mO(C_2H_4O)_nH$$

wherein $CH_3(C_2H_4)_m$ is a short chain linear alkyl having from about 3 to 23 or fewer carbon atoms (i.e., m can be in the range from about 1 to 11 carbon atoms), and n is in the range from about 5 to 25.

Another example is short chain nonionic polyoxypropylenes having the general formula:

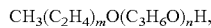

wherein $CH_3(C_2H_4)_m$ is a short chain linear alkyl having from about 3 to 23 or fewer carbon atoms (i.e., m can be in the range from about 1 to 11 carbon atoms), and n can preferably be in the range from about 5 to 25.

Exemplary short chain linear alcohol ethoxylate surfactant are commercially available, for example, under the trade names "SURFONIC L12-6" from Huntsman, Austin, Tex., "SURFONIC L24-7" from Huntsman, Austin, Tex., "TERGITOL 15-S-7", "TERGITOL 24-L-60", "ALPHONIC 1012-60", "ALPOHONIC 1414-60", "BIOSOFT ET 630," from Stepan Company, Chicago, Ill., and "GENOPAL 24-L-60."

Other exemplary surfactants include polyethylene glycol, fatty acid ethoxylates, phosphate esters, octyl phenol ethoxylates, and nonyl phenol ethoxylates.

Useful polyethylene glycol surfactants are commercially available, for example, under the trade names "ADEKA PEG" from Asahi Denka Kogyo, Tokyo, Japan.

Useful fatty acid ethoxylate surfactants are commercially available, for example, under the trade names "NINEX MT-610", "NINEX MT-615", and "NINEX MT-630" from Stepan, Northfield, Ill.

Useful phosphate ester surfactants are commercially available, for example, under the trade names "STEPFAC 8180", "STEPFAC 8181", and "STEPFAC 8182" from Stepan.

Useful octyl phenol ethoxylate surfactants are commercially available, for example, under the trade name "MAKON OP-9" from Stepan, Northfield, Ill.

Useful nonyl phenol ethoxylate surfactants are commercially available, for example, under the trade names "MAKON 4", "MAKON 6", "MAKON 8", "MAKON 10", "MAKON 12", and "MAKON 14" from Stepan, Northfield, Ill.

A cationic surfactant is a surface-active molecule in which an active portion of a lipophilic portion of the molecule forms a positive ion (i.e., cation) when placed in aqueous solution. In one embodiment, exemplary cationic surfactant includes ethoxylated tallow amine.

The amount of surfactant ("surfactant" refers to one or a combination of surfactants) can be any amount that will allow the preparation of a suspension concentrate. Useful amounts of surfactant will be apparent to the skilled artisan based on this overall description, with exemplary amounts being below about 20 percent by weight surfactant based on the total weight of suspension concentrate, such as in the range from about 0.1 or 1 to about 10 or 15 weight percent surfactant based on the total weight of the suspension concentrate with a particularly preferred range being from 0.5 to 3 weight percent.

A dispersant can also be useful to facilitate preparation of a suspension concentrate containing glyphosate acid particles. A dispersant can stabilize and maintain a separation between the suspended particles, which otherwise may have a tendency to flocculate due to attractive forces. Dispersants can provide repulsive forces to balance the tendency to flocculate. An example of a useful type of dispersant is a nonionic dispersant such as Tersperse 4892 from Huntsman. Other examples of dispersants are listed in the table above.

The amount of dispersant can be any amount that will allow the preparation of a suspension concentrate, and that may help to stabilize a suspension concentrate, e.g., by preventing flocculation. Useful amounts may depend on the type of dispersant and the composition of the suspension concentrate, as will be apparent to the skilled artisan. Exemplary amounts of dispersant can be below about 10 or 8 percent by weight dispersant based on the total weight of the suspension concentrate, with preferred amounts being from about 2 to about 6 weight percent dispersant based on the total weight of the suspension concentrate.

Other ingredients, additives, or adjuvants can also be included in the suspension concentrate, as will be appreciated by those skilled in the relevant arts. For example, an antifreeze may be useful, such as propylene glycol or other low molecular weight alcohols or polyols, in an amount to reduce the freezing point of the suspension concentrate. The amount of the antifreeze can be any amount that is useful, as will be understood by the skilled artisan. Exemplary amounts of antifreeze can be below about 20 weight percent based on the total weight of the suspension concentrate, for example from 1 to about 15 weight percent, or from about 5 to about 10 weight percent.

Thickeners can be included in the suspension concentrate to provide gravitational stabilization by increasing viscosity. Useful thickeners include chemical compounds and polymeric materials that will be known to and understood by the skilled artisan, and include, generally, natural and synthetic starches, gums, and other types of chemical compounds that will increase the viscosity of a solution. Thickening agents are well known in the chemical and polymer arts, and include, inter alia, polyacrylamides, cellulosic resins and functionalized cellulosic resins, polyacrylic acids, polyethylene oxides, and the like. Commercially available examples include Kelzan and Rhodaopl 23 xanthan gums, Attagel 50 and Attaflow FL clays, Carbopol 910 polyacrylic acid polymer, Kelcosol sodium alginate, and Bentolite purified Bentonite.

A useful amount of thickener will result in increased viscosity and stability, without causing viscosity build that would be excessive for application of the composition as a herbicide. Amounts below about 5 or 10 weight percent, based on the total weight of the suspension concentrate, may generally be useful. Preferred amounts may be less 0.5 weight percent for gums or cellulose resins.

Another ingredient in a suspension concentrate can be an antifoaming agent. Antifoaming agents are well understood in the chemical and herbicide arts, and a variety of useful examples are commercially available. Antifoam agents are substances such as silicones, organic phosphates, and alcohols, which inhibit the formation of bubbles in a liquid by reducing surface tension. One specific example of a commercially available antifoam agent is SAG 10 (a 10% silicone in water), from Witco OSI. The amount of antifoaming agent used in a suspension concentrate will also be apparent to the skilled artisan, with typical amounts being less than 1 percent by weight, e.g., less than 0.5 percent by weight.

Other useful additives or adjuvants to the suspension concentrate may include other surfactants, antimicrobial agents, anticorrosion agents, and other ingredients that will be understood to be useful, in amounts that will also be understood. Surfactants having functions of wetting, spreading, or penetrating, preferably to improve efficacy of a herbicide composition, may also be added to the formulation or can be added when a tank mix is made for application. Organic solvents may be included in the suspension concentrate if desired, but are generally not used or needed.

The ingredients can be combined by known methods, including mixing, agitating, and dispersing, and, if needed or otherwise desired, milling of the glyphosate acid particles, to produce a suspension concentrate. Any of the mixing, milling, agitating, dispersing, or combining steps can be done in any order, such as milling the glyphosate acid particles and adding the milled particles to water and other ingredients, or by adding the particles to water and other ingredients followed by wet milling.

One exemplary method of producing a suspension concentrate starts with glyphosate acid particles in the form of a wet cake or dry (granular, powder) acid, generally having a relatively large particle size (e.g., greater than about 10 microns). The wet cake or dry particles of that size can be mixed or dispersed into a liquid. This can be done, for example, by combining the glyphosate acid particles with water and other ingredients with agitation or mixing to disperse the particles. For example, the glyphosate acid particles can be added to water and one or more of surfactant, dispersant, antifreeze, and antifoam, and mixed using a high-speed mixer to disperse the glyphosate acid particles. The mixture of glyphosate acid, water, and other ingredients can be further processed toward a suspension concentrate by methods that will process the glyphosate acid particles into a form that allows suspension of the particles in water in the form of a suspension concentrate, for instance by reducing the size of the particles in the presence of a useful surfactant. Thus, a processing step can be to reduce the size of glyphosate acid particles to a size that will allow the particles, in combination with one or more of the other ingredients described herein such as surfactant and/or dispersant, to be maintained in a stable suspension concentrate composition. An exemplary method of reducing the size of the glyphosate acid particles is by using milling techniques, e.g., what is referred to as "wet milling." A typical such average particle size can be below about 10 microns, for example in the range from about 4 to about 8 microns or from about 5 to about 7 microns. Any method of reducing particle size may be useful, such as by using an attrition mill, ball mill, sand mill, or other milling process.

After reduction of the particle size, the solution containing the suspended glyphosate acid particles can be further combined with a thickener, by mixing the thickener into the solution.

The suspension concentrate can preferably be stable in the form of a suspension concentrate for a useful period, meaning that the suspension concentrate composition does not settle or otherwise transform out of the suspension concentrate form, and maintains the form of a suspension concentrate, for a useful amount of time. Useful periods of stability can depend on timing, e.g., between preparation, further processing of, and use (application) of the suspension concentrate, which time periods may vary greatly based on convenience, preference, inherent stability of the suspension, or other factors. If a suspension concentrate or a derivative form of the suspension concentrate can be applied in a short or very short period of time after preparation, longer-term stability is not required. Exemplary suspension concentrates of the invention have been found to be stable at approximately room temperature and in substantially undisturbed and un-agitated environments for periods in excess of 6 or 12 months. Longer or shorter periods would also be useful.

The suspension concentrate can be applied directly to a field or plant to control undesired plant growth, or can be combined with other ingredients to form a derivative herbicide composition for application which can be applied to a field or plant, e.g., as a "herbicide application composition" to control undesired plant growth. "Herbicide application composition" refers to a herbicide composition having a concentration of herbicide compound (here, glyphosate acid) that would normally be applied to a field or plant to control undesired plant growth, as opposed, for example, to compositions having higher concentrations of herbicide compound that sometimes occur in preparation, storage, shipping, or sale of a herbicide composition. It is noted that suspension concentrate compositions as described herein are capable of controlling plant growth if applied directly to a plant. Yet it can be typical for reasons of efficiency, cost, convenience, techniques presently used in applying herbicide compositions, and environmental considerations, to use a relatively diluted form of herbicide compositions to conveniently apply a specific and known amount of herbicide compound per acre or per other unit of application. By way of example, herbicide application compositions include any herbicide composition having such a specific concentration of glyphosate acid for application, e.g., to a field, and specifically include suspension concentrates and derivatives prepared by combining the suspension concentrate with one or more of water, acidifying agent, another herbicide, or other ingredients, as will be described in more detail below.

Additional ingredients can be added to the suspension concentrate to produce a derivative herbicide composition or herbicide application composition. These added ingredients may be (useful in the herbicide composition for purposes of dilution, stability, pH adjustment, anti-foaming, or to otherwise facilitate application or increase efficacy. These other ingredients may be added to the suspension concentrate or derivative herbicide composition at any time and in any order, as desired or convenient. Exemplary additional ingredients include water, antifoaming agents, acidifying agents, anticorrosion agents, or additional active herbicide compounds, such as described, for example, in Applicants' copending U.S. patent application entitled "Herbicide Compositions Comprising Imidazolinone Acid, Methods of Preparation, and Methods of Use,", U.S. Ser. No. 10/103,519, filed on even date herewith and incorporated herein by reference.

A preferred embodiment of a herbicide composition of the invention, comprising or prepared from a suspension concentrate comprising glyphosate acid, can further include acidifying agent, particularly an acidifying agent that improves the efficacy of the herbicide composition. Examples of a certain type of acidifying agent are described in U.S. Pat. Nos. 4,445, 925, 4,994,101, 5,288,692, (Young) the disclosures of which are incorporated herein by reference. Other exemplary acidifying agents are known, and still others are described in Assignee's copending United States Patent Application entitled "Herbicide Composition Comprising Herbicide Compound in Acid Form and Acidifying Agent," having U.S. patent application Ser. No. 10/102,799, filed on even date herewith, and incorporated herein by reference. See also Assignee's copending United States Patent Application entitled "Herbicide Microemulsion-Forming-Concentrates, Microemulsions, and Methods,"U.S. patent application Ser. No. 10/103,455, filed on even date herewith, and incorporated herein by reference. A preferred herbicide application composition can be formulated to include an acidifying agent, and most preferably to include sufficient acidifying agent to exhibit a pH that is below about 2.6, preferably below about 2.3, e.g., below the pKa of glyphosate acid.

While wishing not to be bound by theory, it is believed that the direct application of the acid form of glyphosate, especially as part of a herbicide composition having a pH below the pKa of the glyphosate acid compound, can effect improvements in plant control by one or both of the following mechanisms. First, a neutral (acid) molecule can have an easier time penetrating a cuticle on a plant, compared to a charged (salt) molecule. Secondly, an acidifying agent and a low pH of a herbicide composition can have a damaging effect on a plant's surface, thereby letting more herbicide penetrate the surface. Also, the neutral acid molecule can be less susceptible to de-activation by hard water.

A variety of different acidifying agents can be useful with the herbicide compositions of the invention. The particular acidifying agent chosen and the amount used can be based on factors including the intended use or application of the herbicide composition (including the identity of the target undesirable plant growth and any nearby desirable plant growth) the method of application, physical and chemical properties of the herbicide application composition, and others. The acidifying agent may be any of a variety of suitable organic or inorganic acids, of any useful strength or concentration, that can be added to a suspension concentrate or a derivative thereof, preferably without causing substantial or undue negative effects such as reaction with an ingredient of the suspension concentrate such as the glyphosate acid, precipitation, etc. It will be understood that an acidifying agent can be in a concentrated or diluted form, as necessary or desirable.

Non-limiting examples of acidifying agents include acids such as sulfuric acid, phosphoric acid, hydrochloric acid, nitric acid, acetic acid (e.g., "glacial" acidic acid), perchloric acid, polyphosphoric acid, acidic adducts such as the sulfuric acid adducts described in U.S. Pat. No. 5,288,692 (Young), especially the adduct of sulfuric acid and urea, or any other acidifying agent that can be used to affect the pH of a herbicide composition, especially to prepare a herbicide composition including glyphosate acid and having a pH below the pKa of glyphosate acid. These and other acidifying agents can be used alone or in combination.

Just one specific example of a useful type of acidifying agent includes adducts of sulfuric acid, and an "amide" according to the formula:

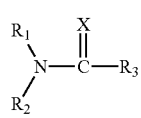

(1)

wherein X is chalcogen, and each of $R_1$, $R_2$ and $R_3$ is independently selected from hydrogen and organic radicals. As used herein, "amide" encompasses all compounds of formula (1) regardless of the chalcogen. The molar ratio of amide to acid is usually in the range of about ¼ to less than 2 so that at least some of the acid is present as the monoamide-acid adduct.

When $R_1$, $R_2$, and $R_3$ are organic radicals, they may be cyclic or acyclic, straight or branched chained, and can contain one or more heteroatoms such as sulfur, nitrogen, oxygen, phosphorus and the like. Further, $R_1$, $R_2$ and $R_3$ can contain one or more substituents such as thiol, hydroxy, nitro, amino, nitrile, amide, ester and halogen groups and others. Such organic radicals may contain aryl groups such as aralkyl and alkaryl groups. Certain preferred organic radicals can be free of olefinic or alkynyl unsaturation and can generally have up to about 20, preferably up to about 10 carbon atoms. Particularly preferred amides include urea, thiourea, formamide, dimethylformamide, biuret, triuret, thioformamide, and combinations of these.

The chalcogens are elements of Periodic Group VI-B and include oxygen, sulfur, selenium, tellurium, and polonium. Oxygen and sulfur can be preferred due to low cost, availability, low toxicity, and chemical activity, and oxygen is the most preferred.

A specific example of an adduct according to formula (1) can be the sulfuric acid/urea adduct:

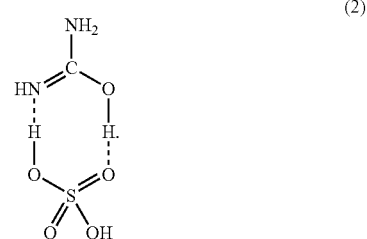

(2)

Other types of useful acidifying agents include various forms of sulfuric acid, phosphoric acid, hydrochloric acid, nitric acid, acetic acid (e.g., "glacial" acidic acid), perchloric acid, polyphosphoric acid, adducts of these, etc. Various such acids are commercially available in different forms and concentrations, such as solids, liquid (aqueous) solutions, concentrated liquid solutions, etc., or can be prepared by one of skill. Any such form of acidifying acid may be useful to reduce the pH of a herbicide composition prepared from or comprising the suspension concentrate, preferably without causing any undue negative affects. The chosen form of acidifying agent may be based on commercial availability, convenience, and the overall desired properties of the herbicide composition, its different ingredients (e.g., the herbicide compound), and its desired method of preparation and use.

The amount of acidifying agent added to a suspension concentrate or herbicide application composition can be based on factors including the particular composition and chemistry of the suspension concentrate or herbicide application composition, including the amounts and chemistries of surfactant and herbicide compound; the amount of water; the type of acidifying agent and its chemistry and strength (concentration); the desired pH; etc. Preferred amounts of any particular acidifying agent can be capable of improving the efficacy of the herbicide composition as applied, and particularly preferred amounts will be sufficient to produce an application composition having a pH below 2.3 or 2.6, or otherwise below the pKa of glyphosate acid compound.

Examples of useful amounts of acidifying agent will be quite varied considering the above factors. Relatively strong concentrations of liquid (aqueous) acidifying agent solutions such as 93% liquid sulfuric acid, 72% phosphoric acid, 85% polyphosphoric acid, 90% nitric acid, 99% glacial acetic acid, etc., can be added directly or can be first diluted and then added to a suspension concentrate or a derivative formulation in an amount to bring the pH below about 3, e.g., below about 2.6 or 2.3, or lower. In terms of volume percent, very generally speaking, useful amounts of aqueous acidifying agent such as those listed above can be below about 5 or 10 volume percent, e.g., in the range from about 0.01 to about 4 parts by volume aqueous acidifying agent based on the total by volume of suspension concentrate and acidifying agent. Volumes of acidifying agent outside of this range may also be useful, depending on the composition and strength of the acidifying agent and the desired pH.

The herbicide compositions can be used for immediate and long-term, post-emergent control of a large variety of different forms of vegetation. As an example, the suspension concentrate could be applied directly to plants for controlling plant growth, although this may include an unnecessarily potent concentration of the glyphosate acid. Furthermore, it may as a general matter be difficult to uniformly apply a small amount of concentrated herbicide composition to a large area without dilution. A suspension concentrate would instead more likely be a product sold commercially as a herbicide concentrate product, which would be a composition that includes a relatively high concentration of glyphosate acid active herbicide compound, as manufactured or packaged for sale, and which may typically be diluted or combined with other ingredients prior to use to form a herbicide application composition.

The suspension concentrate could be purchased by distributors or suppliers, or directly by consumers such as farmers, any of which could add optional ingredients such as water, an acidifying agent (e.g., in the form of a solid, powder, or an aqueous solution, etc.), or another type of herbicide formulation or herbicide compound, to the suspension concentrate. The additional ingredients could, for example, be added and mixed in a tank immediately prior to application. The suspension concentrate would typically be diluted with water. A typical dilution would be 1 pint of suspension concentrate in 15 gallons of water for ground application. Another typical dilution would be 1 pint of suspension concentrate in 3-5 gallons of water for application by air.

In one embodiment of a distribution system, a suspension concentrate could be sold to farming product or nursery dealers, or the like, who could dilute the suspension concentrate with water and/or add other ingredients such as an acidifying agent or other herbicide. This could be particularly convenient if such a dealer normally kept a stock of acidifying agent such as phosphoric acid or sulfuric acid, etc. The suspension concentrate combined with acidifying agent by the dealer could be sold to an end consumer who could use the composition as purchased or who could optionally further dilute the purchased composition or add other ingredients to the purchased composition such as an additional herbicide by tank mixing.

Alternatively, the suspension concentrate could be sold directly to end users who could add one or more of the additional ingredients in a tank mixing process. For example, the suspension concentrate could be combined with water or an acidifying agent or both, in a tank, by a farmer, and then applied.

The herbicide compositions can be applied for immediate vegetation control by contact killing, by application of a herbicide application composition to plants. As will be understood by the skilled artisan, herbicide application compositions as described can contain a useful amount of the glyphosate acid active herbicide compound, based on factors of efficacy, safety, application rate, etc. Similarly, a useful amount of herbicide application composition (containing the useful amount of glyphosate acid) to be applied to a plant or a field, will be readily understood by those of skill, based, e.g., on desired efficacy, safety, application rate, and environmental factors, etc.

The particular amount of glyphosate acid in any specific herbicide application composition will depend on factors known and as described above. Advantageously, it has been found that certain preferred herbicide application compositions of the invention, especially those that include an acidifying agent, and in particular those that also have a reduced pH, e.g., below about 3, 2.6, or 2.3, can be applied at lower dosages or "application rates" (lower amounts of herbicide compound per plant or per acre) relative to other herbicide compositions containing other forms of glyphosate (e.g., the salt form), or not at a reduced pH as described.

Examples of dosages ("application rates") of glyphosate acid, especially as included in a herbicide compositions of the described pH, to a field, can be in the range from about 1/100 to about 6 pounds glyphosate acid per acre, with dosages in the range from about 0.03 to 0.5 pounds per acre being particularly preferred. More resistant plants or different field environments may require higher concentrations and/or higher dosage rates. The preparation of herbicide application compositions suitable to apply useful dosages, based on the concentration of herbicide compound in a suspension concentrate, will be understood by one of ordinary skill.

The herbicide compositions can, as indicated, be applied using conventional aerial or ground spray techniques in field applications. The herbicide compositions can also be applied by any other useful technique, such as by spot-application to undesired plant growth using a hand-held applicator, or the like.

Advantageously, herbicide compositions of the invention have been found to exhibit the additional advantages of being relatively non-volatile. The advantage of non-volatile herbicide compositions are self-evident to those of skill in the herbicide arts. A non-volatile herbicide composition has the advantage of not evolving, or evolving to a reduced degree, through the air, to inadvertently contact desired plant growth. In practical effect, this advantageous property allows the herbicide compositions of the invention to be applied to undesired plant growth in greater strength or in closer proximity to desired above-ground plant growth.

Vegetation that can be controlled using the herbicide compositions of the invention include any type of vegetation that is or is known to be controlled by glyphosate or glyphosate acid herbicide compounds. The ingredients of the herbicide compositions, e.g., surfactant, dispersant, acidifying agent, etc., can be selected in view of the type of control desired (i.e. pre-emergent or post-emergent) and the type of vegetation to be controlled according to the known attributes of glyphosate compounds, including glyphosate acid.

EXAMPLES

A typical suspension concentrate containing 3 lb glyphosate acid per gallon can be prepared as described herein, from ingredients including:

| Water | 41.60% | |
|---|---|---|
| SAG 30 Antifoam | 0.30 | |
| Propylene Glycol | 5.00 | |
| Surfonic T-15 | 8.00 | tallow amine 15 mole |
| 86% glyphosate wc | 36.10 | wet cake |
| Terspserse 4984 | 2.00 | dispersant |
| 2% Kelzan 0.5% Proxel | 7.00 | |

Other exemplary suspension concentrate formulations may also include a higher amount of surfactant (e.g., 8% by weight or greater) and can have a glyphosate acid concentration of 4 pounds per gallon, as follows:

| Water | 32.45% | |
|---|---|---|
| SAG 30 | 0.30 | antifoam |
| Propylene Glycol | 8.00 | antifreeze |
| AU-392 | 8.00 | nonionic/tallow amine blend |
| Glyphosate WC, Dow | 45.30 | active, 39.0% glyphosate acid |
| Terspserse 4894 | 2.00 | dispersant |
| 2% Kelzan-0.5% Proxel | 4.00 | thickener & antimicrobial |
| Total | 100.00 | |

Glyphosate Acid Content of this formulation:
39.0% w/w
480 g/L
4.0 lb/gal

In the above formulation, the 8% surfactant provides wetting for the preparation of the suspension concentrate, and upon dilution in water functions as an adjuvant to improve efficacy of the herbicide formulation. As another example of ingredients of a suspension concentrate:

| | | |
|---|---|---|
| Water | 32.45% | |
| SAG 30 | 0.30 | antifoam |
| Propylene Glycol | 8.00 | antifreeze |
| LI-700 | 8.00 | lecithin derivative |
| Glyphosate WC, Dow | 45.30 | active, 39.0% glyphosate acid |
| Tersperse 2500 | 2.00 | dispersant |
| 2% Kelzan-0.5% Proxel | 4.00 | thickener & antimicrobial |
| Total | 100.00 | |

Examples 1-5

The following examples illustrate how suspension concentrates of the invention can be used to control plant growth, optionally with an acidifying agent.

Materials and Methods:

Experiments were conducted to evaluate the efficacy of a variety of different types of herbicide formulations, including formulations from suspension concentrates, and to evaluate the effect of adding acids to the spray solution as an adjuvant (see Data Tables for Experiment 2 and Experiment 5). Each treatment in the experiment was replicated three times. An untreated control was also included in each experiment.

Experiment one was designed to identify useful acid concentrations of four acids when used with a 2,4-D acid (2,4-dichlorophenoxy acetic acid) formulation (PCC-1133), or a glyphosate (N-(phosphonomethyl)glycine) acid formulation (PCC-1168 suspension concentrate containing glyphosate acid), in a greenhouse. These treatments were compared to standard 2,4-D and glyphosate formulations (ROUNDUP ULTRA, SABER, SALVO), and an untreated control.

Experiment two determined the effect of adding four different acid adjuvants to five formulations of glyphosate: RODEO, ROUNDUP, ROUNDUP ULTRA, ENGAME, and PCC-1168, at four different glyphosate rates. (The Kochia for experiment 2 did not germinate well.)

Experiment five compared the efficacy of the glyphosate acid formulation PCC-1168, to PCC-1168 containing a variety of acidifying agents.

| PCC-1168 Suspension Concentrate Formulation | | |
|---|---|---|
| INGREDIENT | % AI-Tech | %/WT |
| Water | | 44.60 |
| SAG 30, OSI, Antifoam | | 0.30 |
| Proplyene Glycol, Antifreeze | | 8.00 |
| Surfonic L12-6, Huntsman, nonionic wetting agent | | 0.50 |
| Glyphosate WC, Dow, Active Ingredient | 86.00 | 36.10 |
| Tersperse 4894, Huntsman, nonionic dispersant/wetter | | 3.50 |
| Gum 2% Kelzan-0.5% Proxel Premix, thickener & antimicrobial | | 7.00 |
| (Delivers 0.14% Kelzan, 0.03% Proxel.) | | |

Add in order listed to cowles high speed mixer stopping prior to Kelzan-Proxel addition.
Grind to 5-18 microns, 4 hrs in attritor, 60%.
Let down to mix tank with scales
Add calculated amount Kelzan/Proxel Premix to milled liquid. Blend moderately for 30 min.

| PCC-1133 Microemulsion Formulation | | |
|---|---|---|
| 2,4-D Acid | 28.0 | 98% 2,4-D acid technical flake |
| Tomadol 1-5 | 32.0 | 11 carbon 5 mole linear alcohol ethoxylate |
| Tomadol 1-7 | 32.3 | 11 carbon 7 mole linear alcohol ethoxylate |
| Rhodofac RS 710 | 8.0 | anionic, phosphate ester surfactant |
| SAG 10 Antifoam | 0.1 | |

The PCC-1133 microemulsion was made by adding surfactants to a mixing vessel and warming to 130F.-150F. Antifoam and acid were added and mix in until clear, with the 2,4-D acid becoming dissolved in the surfactant, producing a MFC. A microemulsion was formed from the MFC by combining 2 ml MFC with 98 ml water with agitation.

Procedure

For each experiment conducted, greenhouse flats 26 cm2 by 6 cm deep were filled with Metro Mix 200 potting soil (experiments one and two) or Metro Mix 350 (experiments three, four, and five). The soil was pre-wetted before filling the flats. Six furrows were pressed into the soil in each flat using a custom designed form. Corn, tame oats, wheat, pinto beans, cotton, and sunflower were planted in each tray. Cottonseed was soaked for three days previous to planting to improve germination. However, germination was still unacceptable and kochia was substituted in experiments two through five. One species was planted in each of the six rows in each flat. Five seeds were planted in each row of corn, bean, and cotton, and sunflower. Six seeds were planted in each row of oat and wheat. Kochia was sprinkled evenly along the row by hand. Each flat was covered with 2 cm of soil and placed in the greenhouse. Greenhouse conditions were 28/20 C. day/night temperatures and 16/8 h day night periods. Light was supplemented with 400 W sodium halide lights.

The plants were allowed to germinate and grow in the greenhouse for 2 weeks and then treated. Treatments were mixed using serial dilutions. In experiment one, the percent acid was reduced in each dilution by one half. In experiments 2 through 5 each dilution reduced the herbicide rate by one half. Acid concentrations were calculated and mixed so that a treatment with one of the acids or LI-136 would have the same amount of acid as the treatment with PCC-1174. Therefore, a treatment designated 4% sulfuric acid would have the same amount of acid as a treatment with 4% PCC-1174.

After mixing in experiments one, four, and five, the pH of the spray solution of each treatment was measured with a, VWR Scientific model 8005 pH meter. The pH was measured to determine if the acid used or the amount of acid added was sufficient to lower the pH below the pKa of the acid herbicides used. The pKa of 2,4-D acid in the PCC-1133 was measured to be 2.87. The pKa of glyphosate acid in PCC-1 168 was measured to be about 2.5 or 2.6.

At the time of treatment, crops were at the following stages: corn-2 to 3 lf, oat-2 to 3 lf, cotton-cotyledon, kochia-7 lf, bean-1st trifoliate, and sunflower-2 to 4 lf. Plants were treated using a greenhouse track sprayer equipped with an 8001E nozzle and calibrated to deliver 140 L ha-1 at the height of the crop canopy. Each treatment was simultaneously applied to three trays of plants, one for each replicate. After treatment, the plants were left in the head house to dry and then transferred to the greenhouse. Plants in each treatment were evaluated visually for injury 1 day, 1 week, and 2 weeks after treatment.

Summary of Variables of Experiments

SUMMARY OF VARIABLES OF EXPERIMENTS

Experiment 1

| Acid Treatments | Volumes of each Acid (v/v %) | Herbicide | Herbicide Rate lb/A | Plants | Reps |
|---|---|---|---|---|---|
| PCC-1174 | 0 | PCC-1133 | 0.125 | dry beans | 3: |
| Sulfuric | 0.125 | PCC-1168 | | wheat | 2 of standards, |
| Phosphoric | 0.5 | | | cotton | 2 of PCC-1133, and 1168 alone = |
| LI-136 | 1 | | | corn | 192 flats |
| | 2 | | | sunflower | |
| | 4 | | | oats | |

Experiment 2

| Treatment | Rates lb/A | Plants | Reps |
|---|---|---|---|
| Rodeo | 0.0313 | dry beans | 3 |
| Roundup | 0.0625 | wheat | |
| Roundup Ultra | 0.125 | kochia (did not germinate) | |
| Engame | 0.25 | corn | |
| PCC-1168 | | sunflower | |
| PCC-1168 + PCC-1174 (4%) | | oats | |
| PCC-1168 + sulfuric (2%) | | | |
| PCC-1168 + phosphoric (2%) | | | |
| PCC-1168 + LI-136 (2%) | | | |

Experiment 5

| Treatment | rates lb/A | Plants | Reps |
|---|---|---|---|
| PCC-1168 | 0.0313 | dry beans | 3 |
| PCC-1168 + Sulfuric (4%) | 0.0625 | wheat | |
| PCC-1168 + HCl (4%) | 0.125 | kochia | |
| PCC-1168 + Nitric (4%) | 0.025 | corn | |
| PCC-1168 + Acetic (4%) | 0.5 | sunflower | |
| PCC-1168 + Phosphoric (4%) | | oats | |
| PCC-1168 + Perchloric (4%) | | | |
| PCC-1168 + Polyphosphoric (4%) | | | |

Following are data that illustrate the efficacy of various herbicide compositions of Experiments 1, 2, and 5. The injury caused by the herbicide treatment was rated visually. Plants were observed and compared to the untreated control. All the plants of each species in each replication were given a single rating. A rating of 0=no injury—the plants look the same as the untreated. A rating of 100=dead—usually highly necrotic, brown and no chance of producing seed.

SALVO® is a commercially available product of Platte Chemical Co. containing 5 lb 2,4-D acid equivalent/gallon as 2-ethyl-hexyl ester of 2,4-D SABER® is 2,4-D formulated as a dimethylamine salt (2,4-dichlorophenoxy dimethylamine salt), i.e., is a commercially available product of Platte Chemical Company containing 3.8 lb 2,4-D acid equivalent/gallon as dimethylamine salt.

RODEO is a soluble liquid water based formulation of IPA, glyphosate, and water, commercially available from MONSANTO, and was used according to the labeling instructions.

RODEO ULTRA is a glyphosate salt herbicide composition commercially available from MONSANTO, and was used according to the labeling instructions.

ENGAME is a soluble liquid water based formulation of glyphosate acid, urea, sulfuric acid, and water, commercially available from ENTEK, and was used according to the labeling instructions.

ROUNDUP and ROUNDUP ULTRA are commercially available IPA glyphosate salt and surfactant herbicide compositions.

Acidifying Agents

HCl 37%

Nitric 70%

Glacial Acetic 100%

Perchloric 60%

Polyphosphoric 100%

PCC-1174

Commercially available as "AMADS," which is urea and $H_2SO_4$ in water:

| Chemical Name | 1-amino methanamide dihydrogen tetraoxosulfate, or sulfuric acid and urea |
|---|---|
| Molecular Formula | $NH_2C(OH)NHSO_4H_2$ |

-continued

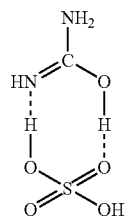

| INGREDIENT | %/WT |
|---|---|
| Water | 22.99 |
| 93% Sulfuric Acid | 48.65 |
| 99% Urea | 26.64 |
| Stepfac 8170 | 1.71 |
| SAG 10 Antifoam | 0.01 |

LI-136=blend of 50 wt. % 21-0-0 urea liquor and 50 wt percent of 72% phosphoric acid in water. The phrase "21-0-0 urea liquor" means a liquid that contains 21% by volume urea (nitrogen), 0% by volume phosphate (phosphorous), and 0% by volume potash (potassium).

Each of the acids were used as is and combined with the PCC-1133 or PCC-1168 herbicide compositions to form a solution that contains 2 percent or 4 percent by volume of the acid solution, as indicated in the data tables, and such that the pH of the herbicide composition was below the pKa of the particular herbicide compound.

The ingredients of the herbicide compositions as applied are listed in the following data tables, and were diluted with water and used at the rates indicated for herbicide ingredients and acidifying agents.

|   |   | Rate | Units | corn | tame oat | spring wheat | dry bean | sunflower |
|---|---|---|---|---|---|---|---|---|
|   | DATA FOR EXPERIMENT 2 (TWO WEEK) | | | | | | | |
| 1 | RODEO | .0313 | LB AE/A | 0.0 | 0.0 | 0.0 | 0.0 | 0.0 |
| 2 | RODEO | .0625 | LB AE/A | 0.0 | 0.0 | 0.0 | 5.0 | 5.0 |
| 3 | RODEO | 0.125 | LB AE/A | 20.0 | 20.0 | 0.0 | 30.0 | 40.0 |
| 4 | RODEO | 0.25 | LB AE/A | 30.0 | 10.0 | 40.0 | 60.0 | 100.0 |
| 5 | ROUNDUP | .0313 | LB AE/A | 0.0 | 0.0 | 0.0 | 0.0 | 0.0 |
| 6 | ROUNDUP | .0625 | LB AE/A | 20.0 | 5.0 | 0.0 | 33.3 | 40.0 |
| 7 | ROUNDUP | 0.125 | LB AE/A | 70.0 | 70.0 | 60.0 | 50.0 | 90.0 |
| 8 | ROUNDUP | 0.25 | LB AE/A | 90.0 | 80.0 | 70.0 | 80.0 | 100.0 |
| 9 | ROUNDUP ULTRA | .0313 | LB AE/A | 20.0 | 0.0 | 0.0 | 0.0 | 0.0 |
| 10 | ROUNDUP ULTRA | .0625 | LB AE/A | 30.0 | 20.0 | 40.0 | 50.0 | 40.0 |
| 11 | ROUNDUP ULTRA | 0.125 | LB AE/A | 90.0 | 49.0 | 70.0 | 70.0 | 90.0 |
| 12 | ROUNDUP ULTRA | 0.25 | LB AE/A | 100.0 | 80.0 | 90.0 | 80.0 | 100.0 |
| 13 | ENGAME | .0313 | LB AE/A | 20.0 | 0.0 | 0.0 | 60.0 | 60.0 |
| 14 | ENGAME | .0625 | LB AE/A | 40.0 | 20.0 | 20.0 | 60.0 | 63.3 |
| 15 | ENGAME | 0.125 | LB AE/A | 50.0 | 40.0 | 30.0 | 60.0 | 90.0 |
| 16 | ENGAME | 0.25 | LB AE/A | 90.0 | 80.0 | 90.0 | 75.0 | 100.0 |
| 17 | PCC-1168 | .0313 | LB AE/A | 0.0 | 0.0 | 0.0 | 0.0 | 0.0 |
| 18 | PCC-1168 | .0625 | LB AE/A | 0.0 | 0.0 | 0.0 | 0.0 | 0.0 |
| 19 | PCC-1168 | 0.125 | LB AE/A | 20.0 | 50.0 | 10.0 | 20.0 | 16.7 |
| 20 | PCC-1168 | 0.25 | LB AE/A | 70.0 | 60.0 | 80.0 | 46.7 | 40.0 |
| 21 | PCC-1168 PCC-1174 | .0313 4 | LB AE/A % V/V | 50.0 | 30.0 | 5.0 | 40.0 | 40.0 |
| 22 | PCC-1168 PCC-1174 | .0625 4 | LB AE/A % V/V | 50.0 | 60.0 | 20.0 | 40.0 | 40.0 |
| 23 | PCC-1168 PCC-1174 | 0.125 4 | LB AE/A % V/V | 70.0 | 60.0 | 70.0 | 63.3 | 76.7 |
| 24 | PCC-1168 PCC-1174 | 0.25 4 | LB AE/A % V/V | 90.0 | 80.0 | 80.0 | 80.0 | 100.0 |
| 25 | PCC-1168 SULFURIC ACID | .0313 2 | LB AE/A % V/V | 10.0 | 10.0 | 10.0 | 40.0 | 5.0 |
| 26 | PCC-1168 SULFURIC ACID | .0625 2 | LB AE/A % V/V | 10.0 | 10.0 | 10.0 | 40.0 | 10.0 |
| 27 | PCC-1168 SULFURIC ACID | 0.125 2 | LB AE/A % V/V | 50.0 | 20.0 | 10.0 | 60.0 | 28.0 |
| 28 | PCC-1168 SULFURIC ACID | 0.25 2 | LB AE/A % V/V | 90.0 | 70.0 | 80.0 | 80.0 | 90.0 |
| 29 | PCC-1168 PHOSPHORIC ACID | .0313 4 | LB AE/A % V/V | 0.0 | 0.0 | 0.0 | 0.0 | 1.7 |
| 30 | PCC-1168 PHOSPHORIC ACID | .0625 4 | LB AE/A % V/V | 0.0 | 0.0 | 0.0 | 20.0 | 5.0 |
| 31 | PCC-1168 PHOSPHORIC ACID | 0.125 4 | LB AE/A % V/V | 5.0 | 5.0 | 5.0 | 40.0 | 40.0 |
| 32 | PCC-1168 PHOSPHORIC ACID | 0.25 4 | LB AE/A % V/V | 60.0 | 60.0 | 40.0 | 60.0 | 80.0 |
| 33 | PCC-1168 LI-136 | .0313 4 | LB AE/A % V/V | 5.0 | 0.0 | 0.0 | 10.0 | 20.0 |
| 34 | PCC-1168 LI-136 | .0625 4 | LB AE/A % V/V | 5.0 | 0.0 | 0.0 | 20.0 | 40.0 |

-continued

| | | Rate | Unit | | | | | |
|---|---|---|---|---|---|---|---|---|
| 35 | PCC-1168 LI-136 | 0.125 4 | LB AE/A % V/V | 20.0 | 0.0 | 10.0 | 40.0 | 70.0 |
| 36 | PCC-1168 LI-136 | 0.25 4 | LB AE/A % V/V | 50.0 | 50.0 | 60.0 | 70.0 | 100.0 |
| 37 | UNTREATED | | | 0.0 | 0.0 | 0.0 | 0.0 | 0.0 |

DATA FOR EXPERIMENT 5 (TWO WEEK)

| | | Rate | Unit | corn | tame oat | kochia | spring wheat | dry bean | sunflower |
|---|---|---|---|---|---|---|---|---|---|
| 1 | PCC-1168 | .0313 | LB AE/A | 0.0 | 0.0 | 0.0 | 0.0 | 5.0 | 0.0 |
| 2 | PCC-1168 | .0625 | LB AE/A | 0.0 | 0.0 | 0.0 | 10.0 | 30.0 | 20.0 |
| 3 | PCC-1168 | 0.125 | LB AE/A | 20.0 | 20.0 | 0.0 | 40.0 | 50.0 | 60.0 |
| 4 | PCC-1168 | 0.25 | LB AE/A | 60.0 | 60.0 | 20.0 | 70.0 | 70.0 | 95.0 |
| 5 | PCC-1168 | 0.5 | LB AE/A | 75.0 | 70.0 | 50.0 | 80.0 | 75.0 | 100.0 |
| 6 | PCC-1168 SULFURIC ACID | .0313 4 | LB AE/A % V/V | 0.0 | 0.0 | 0.0 | 10.0 | 50.0 | 60.0 |
| 7 | PCC-1168 SULFURIC ACID | .0625 4 | LB AE/A % V/V | 10.0 | 30.0 | 0.0 | 30.0 | 70.0 | 90.0 |
| 8 | PCC-1168 SULFURIC ACID | 0.125 4 | LB AE/A % V/V | 65.0 | 60.0 | 10.0 | 65.0 | 80.0 | 95.0 |
| 9 | PCC-1168 SULFURIC ACID | 0.25 4 | LB AE/A % V/V | 80.0 | 75.0 | 50.0 | 85.0 | 85.0 | 100.0 |
| 10 | PCC-1168 SULFURIC ACID | 0.5 4 | LB AE/A % V/V | 100.0 | 100.0 | 95.0 | 100.0 | 98.0 | 100.0 |
| 11 | PCC-1168 HYDROCHLORIC ACID | .0313 4 | LB AE/A % V/V | 0.0 | 0.0 | 0.0 | 0.0 | 30.0 | 20.0 |
| 12 | PCC-1168 HYDROCHLORIC ACID | .0625 4 | LB AE/A % V/V | 0.0 | 0.0 | 0.0 | 10.0 | 50.0 | 65.0 |
| 13 | PCC-1168 HYDROCHLORIC ACID | 0.125 4 | LB AE/A % V/V | 10.0 | 25.0 | 0.0 | 40.0 | 60.0 | 70.0 |
| 14 | PCC-1168 HYDROCHLORIC ACID | 0.25 4 | LB AE/A % V/V | 75.0 | 70.0 | 10.0 | 60.0 | 80.0 | 90.0 |
| 15 | PCC-1168 HYDROCHLORIC ACID | 0.5 4 | LB AE/A % V/V | 80.0 | 90.0 | 60.0 | 90.0 | 93.0 | 100.0 |
| 16 | PCC-1168 NITRIC ACID | .0313 4 | % V/V LB AE/A | 0.0 | 0.0 | 0.0 | 0.0 | 50.0 | 50.0 |
| 17 | PCC-1168 NITRIC ACID | .0625 4 | % V/V LB AE/A | 0.0 | 0.0 | 0.0 | 10.0 | 55.0 | 65.0 |
| 18 | PCC-1168 NITRIC ACID | 0.125 4 | % V/V LB AE/A | 15.7 | 25.0 | 10.0 | 40.0 | 60.0 | 75.0 |
| 19 | PCC-1168 NITRIC ACID | 0.25 4 | % V/V LB AE/A | 75.0 | 70.0 | 60.0 | 60.0 | 80.0 | 90.0 |
| 20 | PCC-1168 NITRIC ACID | 0.5 4 | % V/V LB AE/A | 80.0 | 85.0 | 60.0 | 85.0 | 90.0 | 98.0 |
| 21 | PCC-1168 GLACIAL ACETIC ACID | .0313 4 | % V/V LB AE/A | 0.0 | 0.0 | 0.0 | 0.0 | 0.0 | 0.0 |
| 22 | PCC-1168 GLACIAL ACETIC ACID | .0625 4 | % V/V LB AE/A | 0.0 | 0.0 | 0.0 | 0.0 | 0.0 | 5.0 |
| 23 | PCC-1168 GLACIAL ACETIC ACID | 0.125 4 | % V/V LB AE/A | 10.0 | 20.0 | 0.0 | 36.7 | 30.0 | 40.0 |
| 24 | PCC-1168 GLACIAL ACETIC ACID | 0.25 4 | % V/V LB AE/A | 60.0 | 60.0 | 0.0 | 70.0 | 50.0 | 60.0 |
| 25 | PCC-1168 GLACIAL ACETIC ACID | 0.5 4 | % V/V LB AE/A | 75.0 | 75.0 | 20.0 | 80.0 | 70.0 | 95.0 |
| 26 | PCC-1168 PHOSPHORIC ACID | .0313 4 | LB AE/A % V/V | 5.0 | 0.0 | 0.0 | 0.0 | 30.0 | 40.0 |
| 27 | PCC-1168 PHOSPHORIC ACID | .0625 4 | LB AE/A % V/V | 15.0 | 0.0 | 5.0 | 0.0 | 40.0 | 65.0 |
| 28 | PCC-1168 PHOSPHORIC ACID | 0.125 4 | LB AE/A % V/V | 60.7 | 60.0 | 10.0 | 65.0 | 50.0 | 60.0 |
| 29 | PCC-1168 PHOSPHORIC ACID | 0.25 4 | LB AE/A % V/V | 80.0 | 75.0 | 20.0 | 85.0 | 70.0 | 95.0 |
| 30 | PCC-1168 PHOSPHORIC ACID | 0.5 4 | LB AE/A % V/V | 93.0 | 95.0 | 80.0 | 95.0 | 98.0 | 100.0 |
| 31 | PCC-1168 PERCHLORIC ACID | .0313 4 | LB AE/A % V/V | 0.0 | 0.0 | 0.0 | 0.0 | 40.0 | 40.0 |
| 32 | PCC-1168 PERCHLORIC ACID | .0625 4 | LB AE/A % V/V | 20.0 | 20.0 | 0.0 | 20.0 | 50.0 | 60.0 |
| 33 | PCC-1168 PERCHLORIC ACID | 0.125 4 | LB AE/A % V/V | 65.0 | 60.0 | 20.0 | 60.0 | 55.0 | 60.0 |
| 34 | PCC-1168 PERCHLORIC ACID | 0.25 4 | LB AE/A % V/V | 80.0 | 75.0 | 30.0 | 75.0 | 60.0 | 95.0 |
| 35 | PCC-1168 PERCHLORIC ACID | 0.5 4 | LB AE/A % V/V | 90.0 | 90.0 | 30.0 | 90.0 | 80.0 | 98.0 |
| 36 | PCC-1168 POLYPHOSPHORIC ACID | .0313 4 | LB AE/A % V/V | 70.0 | 70.0 | 0.0 | 60.0 | 50.0 | 50.0 |

| | | -continued | | | | | | |
|---|---|---|---|---|---|---|---|---|
| 37 PCC-1168 POLYPHOSPHORIC ACID | .0625 4 | LB AE/A % V/V | 75.0 | 75.0 | 0.0 | 75.0 | 55.0 | 65.0 |
| 38 PCC-1168 POLYPHOSPHORIC ACID | 0.125 4 | LB AE/A % V/V | 80.0 | 80.0 | 30.0 | 90.0 | 60.0 | 90.0 |
| 39 PCC-1168 POLYPHOSPHORIC ACID | 0.25 4 | LB AE/A % V/V | 95.0 | 90.0 | 40.0 | 93.0 | 85.0 | 95.0 |
| 40 PCC-1168 POLYPHOSPHORIC ACID | 0.5 4 | LB AE/A % V/V | 98.0 | 95.0 | 80.0 | 95.0 | 90.0 | 100.0 |
| 41 UNTREATED | | | 0.0 | 0.0 | 0.0 | 0.0 | 0.0 | 0.0 |

We claim:

1. A herbicide application composition comprising
   a suspension concentrate comprising glyphosate acid, and
   acidifying agent in an amount so the pH of the herbicide application composition is below the pKa of glyphosate acid.

2. The composition of claim 1 wherein the pH of the herbicide application composition is below about 2.6.

3. The composition of claim 1 wherein the herbicide application composition does not contain sulfuric acid.

4. The composition of claim 1 comprising acidifying agent selected from the group consisting of: hydrochloric acid, nitric acid, acetic acid, phosphoric acid, polyphosphoric acid, perchloric acid, and combinations thereof.

5. The composition of claim 1 comprising:
   about 10 to about 100 parts by volume suspension concentrate comprising
      about 20 to about 50 parts by weight glyphosate acid,
      about 5 to about 30 total parts by weight of one or more of surfactant, thickener, antifreeze, and antifoam,
      about 20 to about 60 parts by weight water; and
   about 1 to about 4 parts by volume aqueous acidifying agent.

6. A method of applying a herbicide application composition, the method comprising
   preparing a herbicide application composition comprising
      a suspension concentrate comprising glyphosate acid,
      acidifying agent in an amount so the pH of the herbicide application composition is below the pKa of glyphosate acid, and
   applying the herbicide application composition to control plant growth.

7. The method of claim 6 wherein the suspension concentrate comprises from about 25 to about 50 parts by weight glyphosate acid.

8. The method of claim 6 wherein the suspension concentrate comprises glyphosate acid particles suspended in water and surfactant.

9. The method of claim 8 wherein the glyphosate acid particles have an average particle size below about 10 micron.

10. The method of claim 6 wherein the suspension concentrate comprises cationic ethoxylated tallow amine surfactant.

11. The method of claim 6 wherein the pH of the herbicide application composition is below about 2.6.

12. The method of claim 6 wherein the acidifying agent is selected from the group consisting of: hydrochloric acid, nitric acid, acetic acid, phosphoric acid, polyphosphoric acid, perchloric acid, and combinations thereof.

13. A method of preparing a suspension concentrate comprising glyphosate acid, the method comprising:
   combining glyphosate acid particles with water, surfactant, and dispersant,
   wet milling the mixture of glyphosate acid particles, water, surfactant, and dispersant to reduce the size of glyphosate acid particles to a size that can be suspended in the water, surfactant, and dispersant, and
   using a high speed mixer to mix the water, glyphosate acid particles, surfactant, and dispersant, to produce a suspension concentrate comprising the glyphosate acid particles.

14. The method of claim 13 wherein the glyphosate acid particles are wet milled to an average particle diameter less than 10 microns.

15. The method of claim 13 further comprising adding a thickener to the suspension concentrate comprising the glyphosate acid particles, and mixing.

16. A method of preparing a herbicide application composition comprising glyphosate acid, the method comprising
   preparing a suspension concentrate composition by a method comprising
      combining glyphosate acid particles with water and one or more of surfactant and dispersant, and
      mixing or agitating the water, glyphosate acid particles, and one or more of surfactant and dispersant, to produce a suspension concentrate containing the glyphosate acid particles, and
   adding acidifying agent in an amount so the pH of the herbicide application composition is below the pKa of glyphosate acid.

17. The herbicide application composition of claim 1 wherein the acidifying agent comprises a sulfuric acid adduct according to the formula:

$$\begin{array}{c} R_1 \quad\quad X \\ \diagdown \quad\;\; \| \\ N\!-\!C\!-\!R_3 \\ \diagup \\ R_2 \end{array}$$

wherein X is chalcogen, and each of $R_1$, $R_2$ and $R_3$ is independently selected from hydrogen and organic radicals.

18. The composition of claim 1 wherein the acidifying agent is an adduct of sulfuric acid and urea.

19. The composition of claim 1 wherein the acidifying agent comprises sulfuric acid.

20. The composition of claim 1 comprising
   suspension concentrate comprising glyphosate acid,
   acidifying agent in an amount so the pH of the herbicide application composition is below the pKa of glyphosate acid, and
   water.

21. The composition of claim 20 wherein the ratio of suspension concentrate to water is in the range from 1 pint of suspension concentration: 3 gallons of water to 1 pint of suspension concentrate: 15 gallons of water.

22. The method of claim 6 wherein the acidifying agent comprises sulfuric acid.

23. The method of claim 6 wherein the herbicide application composition comprises
    suspension concentrate comprising glyphosate acid,
    acidifying agent in an amount so the pH of the herbicide application composition is below the pKa of glyphosate acid, and
    water.

24. The method of claim 23 wherein the ratio of suspension concentrate to water is in the range from 1 pint of suspension concentration: 3 gallons of water to 1 pint of suspension concentrate: 15 gallons of water.

25. The method of claim 16 wherein the acidifying agent comprises sulfuric acid.

26. The method of claim 16 comprising a step of diluting the suspension concentrate with water to provide the herbicide application composition.

27. The method of claim 26 wherein the ratio of suspension concentrate to water is in the range from 1 pint of suspension concentrate: 3 gallons of water to 1 pint of suspension concentrate: 15 gallons of water.

28. The method of claim 16 wherein the acidifying agent is added to the suspension concentrate in an amount so the pH of the herbicide application composition is below the pKa of glyphosate acid.

* * * * *